(12) United States Patent
Matusch

(10) Patent No.: US 7,959,599 B2
(45) Date of Patent: Jun. 14, 2011

(54) DISPOSABLE INJECTOR WITH DUAL-PISTON DUAL-CHAMBER SYSTEM

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 12/802,033

(22) Filed: May 29, 2010

(65) Prior Publication Data

US 2010/0249697 A1    Sep. 30, 2010

Related U.S. Application Data

(63) Continuation-in-part of application No. PCT/EP2008/010250, filed on Dec. 4, 2008.

(30) Foreign Application Priority Data

Jan. 1, 2008 (DE) .......................... 10 2008 003 103

(51) Int. Cl.
*A61M 5/30* (2006.01)
(52) U.S. Cl. ......................................................... 604/68
(58) Field of Classification Search ............... 604/68, 604/134, 135
See application file for complete search history.

(56) References Cited

U.S. PATENT DOCUMENTS

| | | | | |
|---|---|---|---|---|
| 5,641,010 A | * | 6/1997 | Maier | 141/329 |
| 2003/0055376 A1 | | 3/2003 | Delay | |
| 2009/0281496 A1 | * | 11/2009 | Matusch | 604/135 |
| 2010/0036326 A1 | * | 2/2010 | Matusch | 604/198 |
| 2010/0076373 A1 | * | 3/2010 | Matusch | 604/68 |
| 2010/0076379 A1 | * | 3/2010 | Matusch | 604/135 |
| 2010/0100040 A1 | * | 4/2010 | Matusch | 604/136 |
| 2010/0106084 A1 | * | 4/2010 | Matusch | 604/68 |
| 2010/0262125 A1 | * | 10/2010 | Matusch | 604/518 |

FOREIGN PATENT DOCUMENTS

| | | |
|---|---|---|
| DE | 19 13 926 A1 | 9/1970 |
| EP | 0 692 235 A1 | 1/1996 |
| GB | WO 96/19252 | 6/1996 |

* cited by examiner

*Primary Examiner* — Nicholas D Lucchesi
*Assistant Examiner* — Aarti B Berdichevsky
(74) *Attorney, Agent, or Firm* — R. S. Lombard; K. Bach

(57) ABSTRACT

The invention relates to a disposable injector with a housing, an injector-side, first cylinder-piston unit—at least intermittently fillable—arranged thereon and an upstream detachable container adapter, wherein the container adapter bears a likewise at least intermittently fillable second cylinder-piston unit. A solvent is stored in the first cylinder-piston unit. In the second cylinder-piston unit there is a freeze-dried active pharmaceutical ingredient. Immediately before use of the disposable injector the solvent is conveyed to the second cylinder-piston unit to the active pharmaceutical ingredient, where a solution forms. This solution is transfer-pumped into the first cylinder-piston unit to then be administered.

The present invention develops a disposable injector which stores a liquid and an active ingredient in each case separately and sterilely and provides a space in which the active ingredient is dissolved for application in the liquid or mixed with the liquid.

9 Claims, 3 Drawing Sheets

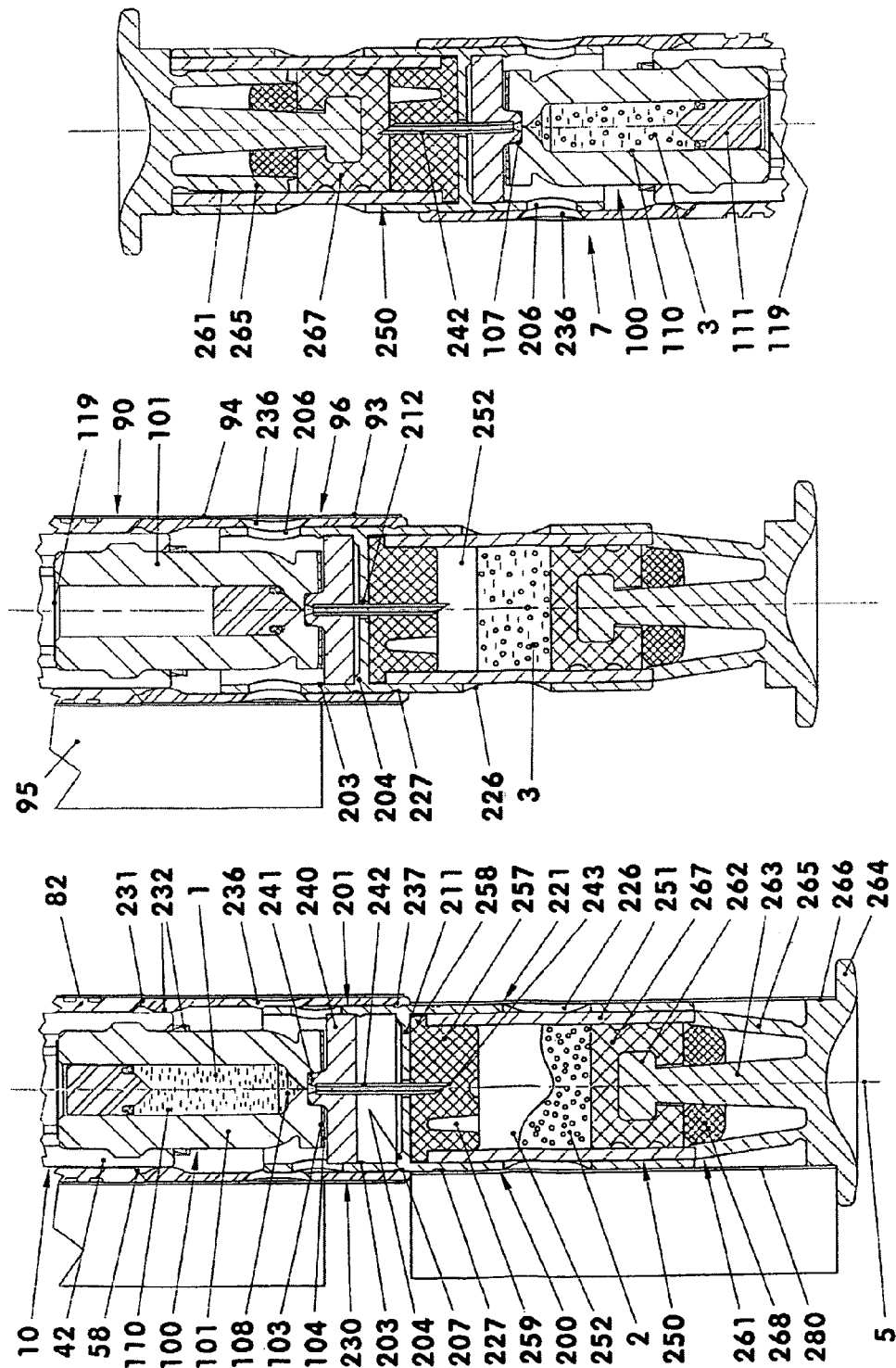

DISPOSABLE INJECTOR WITH DUAL-PISTON DUAL-CHAMBER SYSTEM

CROSS-REFERENCE TO RELATED APPLICATION

This is a continuation-in-part application of pending international application PCT/EP2008/010250 filed Dec. 4, 2008 and claiming the priority of German Application No. 10 2008 003 103.8 filed Jan. 1, 2008.

BACKGROUND OF THE INVENTION

The invention relates to a disposable injector with a housing, an injector-side, first cylinder-piston unit—at least intermittently fillable—arranged therein and an upstream detachable container adapter of the latter, wherein the container adapter bears a likewise at least intermittently fillable second cylinder-piston unit.

WO 96/19252 discloses a system with two cylinder-piston units designed for an injector. The injector-side, first cylinder-piston unit stores the active ingredient, while the upstream second cylinder-piston unit is filled with a solvent. The solvent is pumped into the injector-side cylinder-piston unit to make the solution. Next the container adapter is separated from the injector.

The aim of the present invention is to develop a modular constructed disposable injector which in each case separately and sterilely stores liquid and an active ingredient and has a space in which the active ingredient for the application is dissolved in the liquid or is mixed with the liquid.

SUMMARY OF THE INVENTION

The invention relates to a disposable injector with a housing, an injector-side, first cylinder-piston unit—at least intermittently fillable—arranged thereon and an upstream detachable container adapter, wherein the container adapter bears a likewise at least intermittently fillable second cylinder-piston unit. A solvent is stored in the first cylinder-piston unit. In the second cylinder-piston unit there is a freeze-dried active pharmaceutical ingredient. Immediately before use of the disposable injector the solvent is conveyed to the second cylinder-piston unit to the active pharmaceutical ingredient, where a solution forms. This solution is transfer-pumped into the first cylinder-piston unit to then be administered. The present invention develops a disposable injector which stores a liquid and an active ingredient in each case separately and sterilely and provides a space in which the active ingredient is dissolved for application in the liquid or mixed with the liquid.

The piston of the first cylinder-piston unit is movably arranged in a suction- and pressure-controlled manner in a cylinder sealed at the back in the delivery state. The container adapter is attached detachably to the disposable injector via a coupling element, in which it is arranged to displaceable longitudinally. The container adapter has an adapter region and a container region, whereby both regions are separated by an intermediate floor with throughhole. Between the intermediate floor and the injector-side cylinder sits a needle holder closely adjacent in the region of the front abutting face of the injector-side cylinder and having an injection needle. In the container adapter the second cylinder-piston unit is arranged at the back, and is tightly sealed on the front side—in the delivery state—with an elastic stopper and on the rear side with a piston secured detachably against running in. The tip of the injection needle terminates sealed in the stopper. The container adapter is mounted displaceably against the needle holder in the coupling element to make a hydraulic connection between the interior space of the injector-side cylinder and the interior space of the other cylinder.

In the method for making a solution from a liquid solvent and an active ingredient in and on a disposable injector prior to making the solution the solvent is stored in an injector-side, first cylinder-piston unit, while the active ingredient is contained in second cylinder-piston unit under vacuum, upstream of the cylinder-piston unit. An injection needle, which is sealed on the second cylinder-piston unit is arranged temporarily in front of the first cylinder-piston unit. To make a connection between the interior space of the injector-side cylinder and the interior space of the other cylinder the second cylinder-piston unit is displaced towards the first cylinder-piston unit when pierced. The solvent flows over into the interior space of the second cylinder-piston unit and dissolves the active ingredient there to form the solution. The solution is pumped into the first cylinder-piston unit with the piston of the second cylinder-piston unit.

In an alternative method the piston of the second cylinder-piston unit is pushed at least 80% into the cylinder. In the remaining cylinder space, in which there is no vacuum, is the e.g. freeze-dried active pharmaceutical ingredient. To now have the solvent flow out of the first cylinder-piston unit into the second during the process, the piston of the second cylinder-piston unit is drawn back to generate negative pressure. If required, it can be locked in its end position, holding a residual negative pressure. The locking is released by previous push-in actuation of the piston to convey the solution into the interior space of the first cylinder-piston unit.

The invention here for example presents a needle-free disposable injector which comprises two cylinder-piston units. A first cylinder-piston unit is integrated in the injector and a second is arranged removably and spatially in front of the injector-side spray nozzle. In the first cylinder-piston unit a solvent, e.g. water for infusion purposes, is stored sterile. In the second cylinder-piston unit is e.g. a likewise sterile packed, freeze-dried active pharmaceutical ingredient. Immediately prior to use of the disposable injector the water is conveyed into the second cylinder-piston unit to the active pharmaceutical ingredient, where a solution, a suspension or an emulsion forms.

This liquid is transfer-pumped into the first cylinder-piston unit to then be able to be injected. No lumps enter the cylinder space of the first cylinder-piston unit during transfer-pumping, guaranteeing a precise injection stream.

The second cylinder-piston unit is placed hydraulically upstream of the first cylinder-piston unit. According to the embodiment it sits spatially in front of the first cylinder-piston unit. The second cylinder-piston unit can however also be arranged to the side of the injector. In this case, e.g. both cylinder-piston units lie parallel next to one another.

BRIEF DESCRIPTION OF THE DRAWINGS

Further details of the invention will emerge from the schematically illustrated embodiments.

FIG. 4 is a sectional enlargement of FIG. 1, the injector-side cylinder interior stores solvent, and the external cylinder space stores a lyophilate;

FIG. 5 is as for FIG. 4, however the solution of solvent and lyophilate is in the external cylinder interior;

FIG. 6 is as for FIG. 4, however the solution is in the injector-side cylinder interior;

DETAILED DESCRIPTION OF THE PARTICULAR EMBODIMENTS

Figure 7:
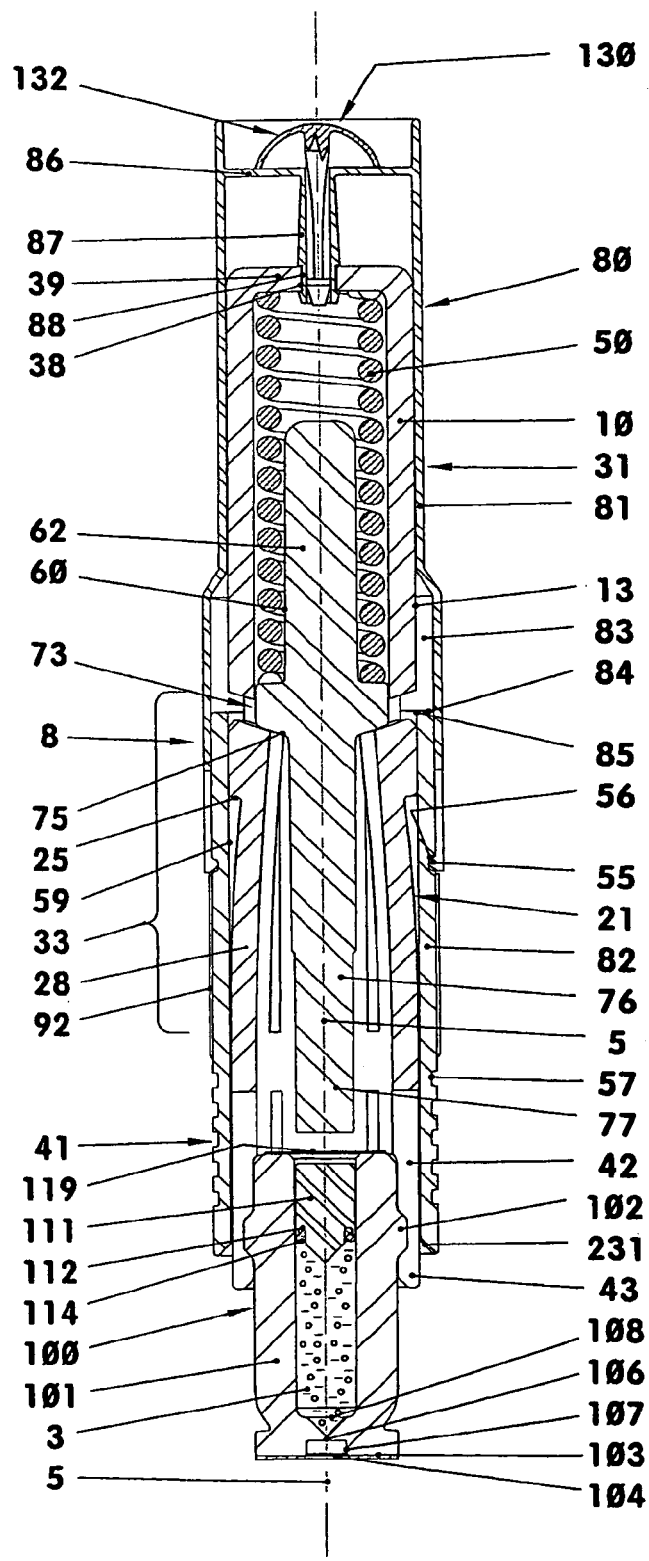
FIG. 7 is as for FIG. 1, however unlocked and actuated.
Figure 8:
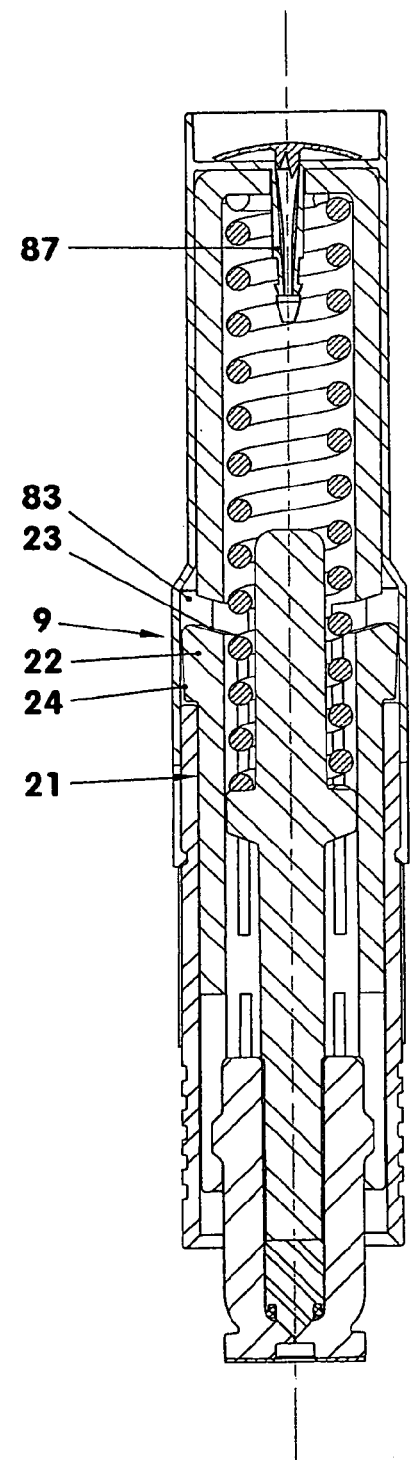
FIG. 8 is as for FIG. 2, however after medicament ejection.

FIGS. 7 and 8 show a disposable injector with a housing (10), in which or on which—in each case at least in certain areas—at least one mechanical spring-loaded energy store, at least one—at least intermittently fillable with active ingredient—cylinder-piston unit (100), at least one piston-actuating plunger (60) and at least one triggering unit (80) is arranged, whereby the spring-loaded energy store (50) comprises at least one pre-tensed spring element, whereby at least part of the piston-actuating plunger (60) is positioned between the spring-loaded energy store (50) and the piston (111) of the cylinder-piston unit (100).

As per FIGS. 1 and 4 to 6 a removable container adapter (200), which likewise stores an at least intermittently fillable cylinder-piston unit (250), is arranged spatially in front of the housing (10) and in front of the cylinder-piston unit (100).

The single-part housing (10) of the needle-free injector is a pot-shaped hollow body open to the bottom with elevated floor (39), as in FIG. 7, and is made from e.g. glassfibre-reinforced polyamide by injection moulding. The housing (10) is subdivided into two functional areas, that is, on the one hand the upper mantle area (31) and on the other hand the lower fixing area (41). In the mantle area (31) the housing (10) has e.g. two opposite windowlike openings (33), as in FIG. 1. On the lower edge of the individual opening (33) a compression bar (21) is respectively mounted articulated.

The compression bars (21) are formed onto the housing (10) and spring outwards as elastic flexional beams (28). The forming site of the compression bars (21) is just above the fixing area (41). A narrow, at least approximately U-shaped gap which encloses the individual compression bar to the side and top is in the mantle section (31) for forming the respective compression bars (21). Over approx. 80% of its length the compression bar (21) has the wall thickness and curve of the walls of the housing (10). In particular, this region also has i.a. the function of the spring-elastic flexional beam (28) and has a sickle-shaped cross-section.

If required, part of this flexional beam (28) can also be equipped with a rectangular cross-section to reduce flexural stresses occurring during use in the flexional beam edge region. In FIG. 8 the compression bar (21) is shown in the undeformed state.

The upper free end here of the individual compression bar (21) is formed by the radially outwards projecting cam (22) which has at least one support surface (23) and one radial bearing face (24). As per FIG. 7 the plunger plate (73) of the tensioned disposable injector lies on the support surface (23) via its collar surface (75). The support surface (23), which here fulfills the function of a wedge face, has the form of a frustum mantle with a tip angle of 120 degrees.

If required, the compression bars (21) or the collar surface (75) at least in the contact area have ceramic armouring or are reinforced e.g. by a stuck-on frustum-mantle-shaped washer.

The bearing surface (24) of the cams (22) of the undeformed flexional beams (28) is part of a frustum mantle, whereof the maximal diameter is e.g. 3 to 4 millimetres greater than the outer diameter of the housing (10), as in FIG. 8. When the disposable injector is tensioned the bearing surface (24) contacts the inner walls (59) of the sleeve-like trigger element (82). The bearing surface (24) has a curve which corresponds to the inner walls (59) for minimizing the surface pressing, if required.

Under the mantle section (31) is the fixing area (41) for accommodating the incorporable cylinder-piston unit (100). The fixing area (41) includes e.g. eight spring hooks (42) aligned parallel to the centre line (5). The spring hooks (42) in each case have an at least two-flank back grip (43) for play-free receiving of the cylinder-piston unit (100). The opposite flanks of the back grip (43) enclose an angle of e.g. 90 degrees of angle. The length and the spring rate of the spring hooks (42) are such that the cylinder (101) can be incorporated without plastic deformation of the spring hooks (42).

Figure 1:
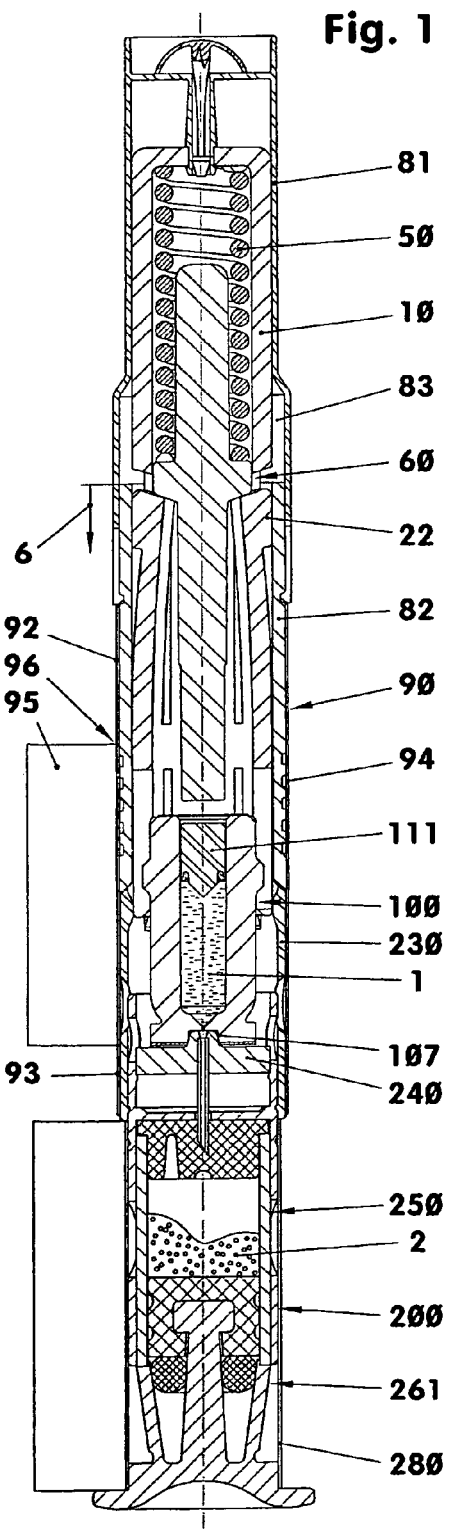
FIG. 1 illustrates a disposable injector with two compression bars and conical collar area.

In the embodiment the cylinder-piston unit (100) comprises a cylinder (101) filled with a liquid solvent (1), as in FIG. 1, in which a piston (111) sits in the rear position. Above the piston (111) in the housing (10) the piston-actuating plunger (60) is arranged e.g. such that it does not touch the piston, however is guided to the side by its lower end into the upper region of the cylinder (101).

The cylinder (101) is e.g. a transparent, thick-walled pot, whereof the cylindrical outer wall bears a for example circumferential detent rib (102), if required, as in FIG. 7, which lies dimensionally stably on the flanks of the back grip (43) of the spring hooks (42). In the for example cylindrical bore of the cylinder (101) sits the rod-less piston (111). The piston (111) has on its front, at least approximately conically configured abutting face an axial annular groove (112) for taking up a sealing ring (114) or a permanently elastic sealing mass. Set into the rear abutting face of the piston (111) if required is an e.g. cylindrical metal plate.

In the centre of the bore of the cylinder (101), whereof the cylinder floor 108 at least approximately matches the contour of the front piston front end, is a short cylindrical, nozzle-like bore (106). Its diameter is approx. 0.1 to 0.5 millimetre. This bore (106) is one to five times as long as its diameter. It terminates in a cylindrical recess (107) of the floor-side outer abutting face (103) of the cylinder (101). This abutting face (103) can be provided with an adhesive ring (104) to additionally boost application safety.

The cylinder (101) is sealed sterile on the rear side with a sterile filter membrane (119).

Between the plunger plate (73) and the elevated floor (39) of the housing (10) the helical compression spring (50) sits pre-tensioned. The resilient force is transferred via the plunger plate (73) to the compression bars (21). Due to the inclination of the collar surface (75) the compression bars (21) are forced radially outwards in the manner of a bevel gear. The outer sleeve (82) permanently supports this radial force.

The piston-actuating plunger (60) has a pilot pin (62) above the plunger plate (73) which pin guides the helical compression spring (50). Underneath the plunger plate (73) centrally in the extension of the pilot pin (62) is the piston slide valve (76) which acts on the piston (111) when the disposable injector is activated. In the embodiment the piston slide valve (76) terminates e.g. 2 to 4 millimetres above the sterile filter membrane (119) of the cylinder-piston unit (100).

The plunger plate (73), is a flat disc, cylindrical at least in certain areas, the outer diameter of which is a few tenths of a millimetre smaller than the inner diameter of the housing (10) in the mantle area (31). The lower front end has a collar surface (75) arranged around the piston slide valve (76). It has the form of a frustum mantle, whose apex angle is about 100 to 130, preferably 120 degrees. The notional tip of the frustum mantle lies on the centre line (5) in the region of the piston slide valve (76). The collar surface (75) can also be curved spherically.

The piston slide valve (76) can of course also be designed as a component separate from the plunger plate (73). For this it is then guided on the inner walls of the housing (10).

In those injectors in which the piston-actuating plunger (60) is guided straight in the housing (10)—at least in sections—with minimal play and the piston-actuating plunger (60) has adequate flexural strength, just a single compression bar (21) also can be used in place of two or more compression bars (21).

The figures illustrate a compression bar-injector with a trigger unit (80) almost fully surrounding the housing (10). Attached to the trigger element (82) is a release cap (81) which encloses the back end of the housing (10), as in also FIGS. 1, 7 and 8.

The trigger element (82) partially enclosing the housing (10) and the cylinder-piston unit (100) is a release sleeve. The substantially cylindrical release sleeve (82), made e.g. from acrylonitrile butadiene styrene, ABS, has on its rear end as abutting face a return flank (84), which here represents a normal plane to the centre line (5) of the injector. The transition between the for example cylindrical inner walls of the trigger element (82) and the return flank (84) is designed e.g. as a sharp edge (85).

In the lower region of the trigger element (82) in its outer wall are several circular grooves (57) or some other comparable structure. The grooves (57) have e.g. comparatively the same distances and extend over 10 to 30 millimetres in length of the trigger element (82).

The release cap (81) is pushed by the back end of the trigger element (82). Directly above the return flank (84) of the trigger element (82) is a widened section (83). With respect to the housing (10) this widened section (83) is positioned and dimensioned precisely such that it can take up the compression bars (21) forced outwards and retreating from the trigger procedure with their cams (22), as in FIG. 8. The inner contour of the widened section (83) is e.g. a circumferential channel.

In place of this widened section (83) partial widened sections or uncovered openings can also be present in the case of a non-rotationally symmetric trigger element (82) per compression bar (21).

According to FIG. 7 the cams (22) lie with their outerlying bearing surfaces (24) on the inner walls (59) of the trigger element (82) as a security. Above the widened section (83) the release cap (81) lies slidably on the outer wall (13) of the housing (10).

For fastening the release cap (81) on the trigger element (82) the trigger element (82) has for example an annular groove (56), in which a circulating web or snap-in cams (55) of the release cap (81) engage. For easier installation the release cap (81) can be slit lengthways e.g. twice in certain areas, as in FIGS. 7 and 8.

At the rear end the release cap (81) has a depressed cap floor (86). Several inwards projecting snap-in pins (87) are formed on the cap floor (86) about a centric bore, for example. At their lower ends in each case the snap-in pins (87) have tab notches (88) which grip round the edge of a central bore (38) of the housing floor (39).

Figure 2:
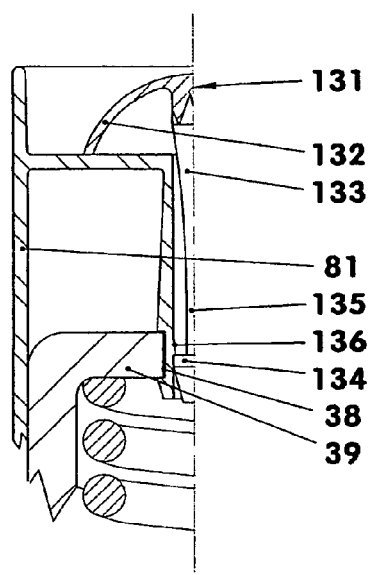
FIG. 2 is a sectional enlargement of FIG. 1.

The snap-in pins (87) are fixed by a pawl (131) of a push-button safety device (130), as in FIG. 2, in the position gripping round the floor (39) in certain areas so that the release cap (81) can move in a longitudinal direction in combination with the trigger element (82) not opposite the housing (10).

The pawl (131) has an elastic, partly calotte-shaped pawl head (132), on which a pawl bolt (133) is formed. The latter bears at its lower, free end a blocking collar (134), which is set down against a waist (135). The blocking collar (134) holds the snap-in pins (87) in their locking position, as in FIG. 2, and latches securely behind a detent link (136).

If the pawl (131) is actuated by being pressed down, the spring-elastic snap-in pins (87) spring behind the blocking collar (134) and are placed on the waist (135). The pawl (131) remains permanently in its actuated position, as in FIG. 8. The new sleeve area of the snap-in pins (87) now has an outer diameter which is smaller than the inner diameter of the bore (38). As a result, the mechanical coupling between the trigger element (82) and the housing (10) is freed.

Figure 3:
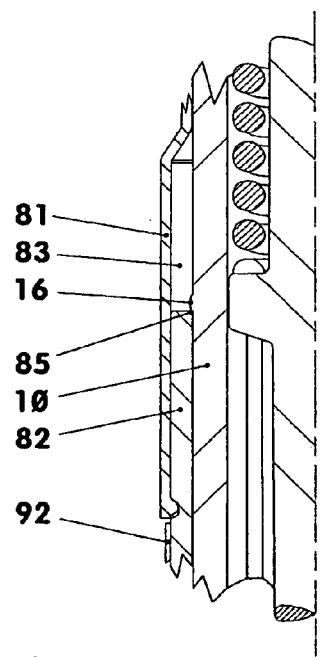
FIG. 3 is a sectional enlargement of FIG. 1, however angularly offset by 90 degrees.

In a region between the cams (22) the housing (10) has a lenticular elevation (16), as in FIG. 3, via which the housing (10) rests on the edge (85) of the trigger element (82) for fixing the housing (10) securely together with the spring element (50) and the piston-actuating plunger (60) during installation in the trigger element (82).

With the housing (10) shown here the support rods (21) have cams (22) with particular back grip flanks (25). These back grip flanks (25) lie at least approximately in a plane normal to the centre line (5) when the support rods (21) are deformed. Accordingly they latch abruptly over the edge (85) when the injector is released. After release they also lie firmly latched on the return flank (85) of the trigger element (82).

The coupling element (230) centred on the cylinder (101) of the cylinder-piston unit (100) rests on the lower e.g. frustum-mantle-shaped abutting face (58), as in FIG. 4, of the trigger element (82). The outer face of the coupling element (230), approximately cylindrical at least in certain areas, has the same outer diameter as the likewise cylindrical outer face of the trigger element (82) in the vicinity of its abutting face (58).

The e.g. cylindrical tubular coupling element (230) sheathes the cylinder (101) not only in certain areas and at the same time lies on the trigger element (82), but is also supported on the housing (10). For this it has in the vicinity of the abutting face (231) several bearing links (232) arranged on the inner wall. The contact links (232) projecting radially inwards are aligned parallel to the centre line (5) and contact the spring hooks (42) of the housing (10).

The coupling element (230) has two opposite windows (236). The windows (236) have a width which corresponds to at least the diameter of the piston (111). The window centres are located at the level of the cylinder floor (108), as in FIG. 6. The inner wall of the coupling element (230) is substantially cylindrical and smooth, forming the guide surface for the container adapter (200). On its lower edge it has e.g. several latch knobs (237) distributed over the periphery. In the guide surface if required is a long link parallel to the centre line (5) and not illustrated here, which engages in a corresponding groove of the container adapter (200) for preventing rotation.

The container adapter (200) is a boxlike component housing a cylinder-piston unit (250) in a container region (221). At the same time it has a sleeve-like adapter region (201) with which it sits longitudinally displaceable in the coupling element (230). On the inside the adapter region (201) guides a needle holder (240) in a longitudinally displaceable manner.

The adapter region (201) is a cylindrical beaker which surrounds the lower fifth of the cylinder (101) with clearance at least according to FIG. 4. It has two opposing e.g. circular windows (206), as in FIG. 5, several, e.g. four stop knobs (203) distributed over the periphery as upper stops for the needle holder (240) and an annular heel (204) on the centrally bored intermediate floor (211). The windows (206) and the previously mentioned longitudinal link of the coupling element (230) can be omitted if the container adapter material is transparent. The longitudinal link can also be omitted if the windows (206) have on the one hand a rectangular form and on the other hand several windows (206) separated from one another only by narrow links are distributed over the periphery.

On its outer wall the adapter region (201) has at the level of the intermediate floors (211) a circumferential notch (207), in which the latch knobs (237) engage, as per FIG. 4.

The needle holder (240) is arranged directly in front of the adhesive foil (104) in front of the front end (103) of the cylinder (101). The latter has a trunnion (241), with which it sits sealingly in the cylinder recess (107). The lower outer edge of the needle holder (240) lies on the stop knobs (203).

A short injection needle (242) sticks centrally, e.g. encapsulated or adhered, into the cylindrical discoid needle holder (240). According to FIG. 4 the injection needle (242) projects right through the bore (212) of the e.g. planar intermediate floor (211) and terminates with its needle tip (243) e.g. in the middle in a stopper (257) laid under the intermediate floor (211).

In the tubular container region (221) there are likewise two or four opposite windows (226). In addition, just in front of the intermediate floor (211) the outer wall has a circumferential notch (227), into which the latch knobs (237) of the coupling element (230) snap, as per FIG. 5. If required, the container region (221) has on the lower end of its outer wall two grip elements, e.g. in the form of a cylinder grip plate standardized according to DIN 13098 part 2.

The cylinder-piston unit (250) is arranged in the container region (221). Its outer diameter is only slightly smaller than the inner diameter of the container region (221). The cylinder-piston unit (250) is e.g. stuck in the container region (221).

The cylinder-piston unit (250) has a cylinder which is formed from a transparent tube (251), e.g. a glass or plastic tube (COC), and an elastic stopper (257). In FIG. 4 the stopper (257), lies at the top, has a flange edge (258), via which it rests axially on the glass tube (251). In the direction of the cylinder interior (252) the stopper (257) has asymmetrical notching (259) which if required is necessary for freeze-drying of the solution of the active pharmaceutical ingredient (2), e.g. a protein, contained in the cylinder-piston unit (250).

According to FIG. 4 the glass tube (251) is sealed on the rear with a mobile piston (261). The piston (261) comprises a piston rod (262), a rear piston pressure plate (264), a front stopper bearer (263) and an elastic piston stopper (267) set on it. To keep the piston (261) in its rear position when the cylinder interior (252) vacuumised, the piston (261) additionally has two or more latching elements (265) which are formed e.g. on the piston pressure plate (264) and are supported—springing elastically outwards—on the rear edge of the glass tube (251). An elastic rubber ring (268) which presses the latching elements (265) outwards sits on the rear side of the piston stopper (267).

In the direction of the glass tube (251) the piston pressure plate (264) has a cylindrical collar (266) having the same outer diameter as the container area (221).

According to FIG. 4 the container region (221) and the piston (261) between the coupling element (230) and the piston pressure plate (264) is pasted over with a peel-off wrapper (280). The peel-off wrapper (280) protectively covers the windows (226) and the latching elements (265) of the piston (261). In addition, the tear-off foil (280) prevents unintentional pushing of the container adapter (200) into the coupling element (230).

To secure the coupling element (230) this, as in FIG. 1, is connected via the wrapper (90) to the trigger element (82) of the injector. The wrapper (90), an originality closure designed as adhesive label, covers almost the entire cylindrical outer wall of the coupling element (230) and the grooves (57) of the trigger element (82).

The wrapper (90) itself is e.g. a paper and/or film strip coated with an adhesive coated on one side in certain areas. The wrapper (90) comprises three separate strips, which in each case can be separated from each other along a perforation (96) or via another predetermined breaking point. The respectively circumferential perforations (96) lie above the grooves (57) and under the windows (206).

The top strip is a rear edge part (92), the middle strip is a tear-off wrapper (94) with a two- to three-centimetre-long tear-off tab (95) and the lower strip is a frontal edge part (93). If the tear-off tab (95) and the tear-off wrapper (94) are unwrapped right around from the trigger element (82) and the coupling element (230) against the adhesion by separating the perforations (96), the coupling element (230) is still held on the injector only via clamping strength.

For the disposable injector to be able to be used the active ingredient (2), e.g. a lyophilate stored in the cylinder-piston unit (250), must be dissolved in the liquid (1), e.g. water for injection purposes, or physiological common salt solution, present in the cylinder (101) of the cylinder-piston unit (100).

For this, the liquid (1) is to be pumped into the container (250).

In a first step the peel-off wrapper (280) is removed from the container region (221) and the container adapter (200) is pushed into the coupling element (230), as in FIG. 5. At this point the injection needle (242) is pressed through the stopper (257) such that the needle tip (243) ends up in the cylinder interior (252). The advance motion of the container adapter (200) is completed when the heel (204) is resting on the needle holder (240). The windows (206) of the container adapter (200) are covered over by the windows (236) of the coupling element (230). The latch knobs (237) latch in the circumferential notch (227).

Through penetration of the injection needle (242) into the cylinder interior (252) the latter communicates via the injection needle (242) with the cylinder interior (110). The vacuum of the cylinder interior (252) sucks the liquid out of cylinder (101) of the cylinder-piston unit (100). Because the rear-side covering of the cylinder (101) is a sterile filter membrane (119) the suctioned piston (111) can follow the liquid (1) and comes to rest on the cylindrical floor (108). In the interior space (252) the lyophilate (2) dissolves in the liquid (1). The dissolution procedure can be observed via the windows (226).

In a second step, as soon as the lyophilate (2) is dissolved, the tear-off wrapper (94) is removed. The grooves (57) of the trigger element (82) thus become visible. Now the injector is positioned such that the cylinder-piston unit (100) lies under the cylinder-piston unit (250), as in FIG. 6. Next, the resulting solution (3) can pumped through the injection needle (242) into the cylinder interior (110). For this the piston (261) is first released by the latching elements (265) being pressed in radially. Due to the residual vacuum the piston stopper (267) is placed on the surface of the solution (3). Light pressure on the piston (261) now transfer-pumps the solution (3) into the cylinder interior (110). The solution (3) pushes the piston (111) along in front of it. Bubble-free filling of the cylinder interior (110) is checked via the windows (206, 236) in the transmitted light. As a rule, a small part of the solution (3) is suctioned back into the glass tube (251) such that the piston (111) is not lying on the sterile filter membrane (119).

In a third step the coupling element (230) is removed up off the housing (10) along with the container adapter (200)—with reference to FIG. 6. The injector still remains secured.

After setting the injector onto the injection site in a last step, e.g. with the thumb of the hand holding the injector, the pawl head (132) must be pressed to move the trigger element (82) together with the release cap (81). The trigger element (82) can now be pushed in the direction of the cylinder-piston unit (100). In this procedure the trigger element (82) glides on the outer wall (13) of the housing (10) linearly down, therefore in the direction of the injection site. The bearing surfaces (24) of the compression bars (21) slip over the edge (85) and under the force of the spring element (50) are released to spring radially outwards into the widened section (83). The compression bars (21) have bent elastically outwards and are now in their actual start position. The now no longer deformed compression bars (21) release the piston-actuating plunger (60) so that the piston slide valve (76) moves abruptly towards the sterile filter membrane (119) of the cylinder (101) under the effect of the spring element (50). The sterile filter membrane (119) is smashed and the piston (111) moves down to empty the cylinder (101), as in FIG. 8. The cylinder (100) is emptied.

In place of a linear sliding motion of the trigger element (82) on the housing (10) a helical motion can also be provided. In this case the trigger element (82) and the housing (10) are guided to one another e.g. via a slide block and a connecting link. If required, release can also be effected by pure swivelling motion between the housing (10) and the trigger element (82). The swivelling axis here would be the centre line (5).

In the variants illustrated in the figures the individual contact zone between the compression bar (21) and the plunger plate (73) is configured as surfaces (23) and (75) which contact each other with a gliding quality. In a particular configuration a roller can be mounted in each face (23) of the individual compression bars (21), which rolls away mounted on an anti-friction bearing, therefore without friction, when the injector is actuated on the face (75) of the plunger plates.

With the exception of the spring element (50), a piston plate present if required and the positioning roller of the support rods (21) present for example, all parts of the previously described disposable injectors are made from plastics or materials similar to plastic or rubber.

LIST OF REFERENCE SYMBOLS 1 water for infusion purposes, solvent
2 lyophilate, active ingredient, active pharmaceutical ingredient
3 injection solution
5 centre line of the injector, longitudinal direction
6 release motion direction of (82), downward motion directional arrow
7 transfer-pump position
8 locked position
9 release position, triggering position
10 housing, single-piece
13 outer surface, cylindrical
16 elevation, lenticular
21 compression bars, support rods
22 cams
23 support surface
24 bearing surface
25 back grip flank
28 flexional beam
31 mantle area
33 openings
38 bore
39 floor
41 fixing area for cylinder-piston unit
42 spring hooks
43 back grip
50 spring element, helical compression spring, spring-loaded energy store
55 snap-in cams
56 annular groove of (82)
57 grooves of (82)
58 abutting face of (82)
59 inner walls of (82)
60 piston-actuating plunger
62 guide pin
73 plunger plate
75 collar surface, conical
76 piston slide
77 piston slide front end, frustum-mantle-shaped
80 trigger unit
81 release cap
82 release element
83 widened section
84 return flank
85 edge, sharp-edged
86 cap floor
87 snap-in pins
88 tab notch
90 originality closure, wrapper, security element adhesive label
92 edge part, behind; label part
93 edge part, front; label part
94 tear-off wrapper
95 tear-off tab
96 perforations, predetermined breaking points
100 cylinder-piston unit, first, injector-side
101 cylinder, injector-side
102 detent rib
103 abutting face
104 adhesive ring
106 bore, nozzle
107 recess in abutting face
108 cylinder floor
110 cylinder interior
111 piston
112 annular groove
114 sealing ring, seal
119 sterile filter membrane
130 push-button safety device, securing element
131 pawl
132 pawl head
133 pawl bolt
134 blocking collar
135 waist
136 detent link
200 container adapter
201 adapter region
203 stop knobs
204 heel, annual
206 windows, on both sides
207 notch, circumferential
211 intermediate floor
212 bore, central
221 container region
226 windows
227 notch, circumferential
230 coupling element, tubular 231 front end
232 bearing links
236 windows
237 latch knobs
240 needle holder
241 trunnion
242 injection needle
243 needle tip
250 cylinder-piston unit, second
251 tube, glass tube, plastic tube
252 cylinder interior
257 stopper, elastic, rubber stopper
258 flange edge
259 notching
261 piston
262 piston rod
263 stopper bearer
264 piston pressure plate
265 latching elements
266 collar
267 piston stopper
268 rubber ring, elastomer spring
280 peel-off wrapper

What is claimed is:

1. In combination with a disposable injector including a housing (10), a cylinder-piston unit (100)—at least intermittently fillable—arranged thereon, an upstream detachable container adapter (200) housing a second cylinder-piston unit (250), the second cylinder-piston unit (250) at least intermittently fillable, the cylinder-piston unit (100) including a piston (111) and an injector-side cylinder (101) having an interior space (110), the improvement which comprises:

the piston (111) of the cylinder-piston unit (100) is movably arranged in a suction- and pressure-controlled manner in the cylinder (101), the cylinder (101) sealed at the back thereof in the delivery state;

the container adapter (200) is attached detachably to the disposable injector via a coupling element (230), in which the container adapter (200) sits displaceable longitudinally;

the container adapter (200) includes an adapter region (201) and a container region (221), an intermediate floor (211) separates the adaptor region (201) from the container region (221), the intermediate floor (211) having throughhole (212) passing therethrough;

between the intermediate floor (211) and the cylinder (101) a needle holder (240) operatively sits, the cylinder (101) having a front abutting face (103) operatively positioned closely adjacent needle holder (240), the needle holder (240) having an injection needle (242) operatively affixed thereto in controllable intermittent fluid communication with the interior space (110) of the cylinder (101);

the second cylinder-piston unit (250) is operatively arranged in the container adapter (200) at the back thereof, an elastic stopper (257) is in tight sealed relationship with the front of the cylinder-piston unit (250)—in a delivery state—and a second piston (261) is secured detachably and against running in at the back of the second cylinder-piston unit (250);

the injection needle (242) has a tip (243) that terminates operatively sealed in the stopper (257) prior to activation;

the second cylinder-piston unit (250) includes a second cylinder (251) having an interior space (252), the container adapter (200) is mounted displaceably against the needle holder (240) in the coupling element (230), the tip (243) of the injection needle (242) is operatively displaceable to pass through stopper (257) and enter interior space (252) of the second cylinder (251), whereby prior to use of the injector for administering to a patient the injection needle (242) upon displacement provides a temporary fluid communication connection between the interior space (110) of the injector-side cylinder (101) and the interior space (252) of the second cylinder (251).

2. The disposable injector according to claim 1, wherein the first cylinder-piston unit (100) further includes a sterile filter membrane (119), the cylinder (101) is sealed gas-permeably in the delivery state proximate the rear thereof with the sterile filter membrane (119).

3. The disposable injector according to claim 1, wherein the needle holder (240) is longitudinally displaceable in the adapter region (201).

4. The disposable injector according to claim 1, wherein on a front side the adapter region (201) encloses the injector-side cylinder (101) at least in certain areas.

5. The disposable injector according to claim 1, wherein the second cylinder-piston unit (250) sits firmly in the container adapter (200).

6. The disposable injector according to claim 1, wherein the second piston (261) of the second cylinder-piston unit (250) includes resilient or spring-loaded latching elements (265) adapted to detachably fix the second piston (261) in an extended position.

7. The disposable injector according to claim 1, wherein the cylinder (101) is transparent, near the cylinder (101) the adapter region (201) has two opposite windows (206) passing therethrough and, the coupling element (230) has two opposite windows (236) passing therethrough, whereby the windows (236) in a solution transferred-pump position of the injector are in front of the windows (206) so that the cylinder interior (110) of the cylinder (101) may be visually checked.

8. The disposable injector according to claim 1, wherein the second cylinder (251) of the second cylinder-piston unit (250) comprises tubular shaped transparent glass, the second piston (261) is in sealed relationship with the back of the second cylinder (251).

9. The disposable injector according to claim 8, wherein the container region (221) has at least two opposite windows (226) passing therethrough in operative alignment with the central region of the transparent second cylinder (251).

* * * * *